(12) United States Patent
Sung

(10) Patent No.: US 10,753,918 B2
(45) Date of Patent: Aug. 25, 2020

(54) PHYSICAL RESERVOIR ROCK INTERPRETATION IN A 3D PETROPHYSICAL MODELING ENVIRONMENT

(71) Applicant: Saudi Arabian Oil Company, Dhahran (SA)

(72) Inventor: Roger R. Sung, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 534 days.

(21) Appl. No.: 14/570,944

(22) Filed: Dec. 15, 2014

(65) Prior Publication Data

US 2016/0169856 A1 Jun. 16, 2016

(51) Int. Cl.
| | | |
|---|---|---|
| *G01N 33/24* | (2006.01) | |
| *G01V 8/00* | (2006.01) | |
| *G01V 11/00* | (2006.01) | |
| *G01V 8/02* | (2006.01) | |

(52) U.S. Cl.
CPC ............... *G01N 33/24* (2013.01); *G01V 8/00* (2013.01); *G01V 8/02* (2013.01); *G01V 11/00* (2013.01)

(58) Field of Classification Search
CPC .... G01V 2210/66; G01V 11/00; G01V 11/10; G01V 8/02; G01V 8/00; G01V 9/002; G01N 33/24; G06K 9/2081; G06K 9/22; G06K 9/64
See application file for complete search history.

(56) References Cited

U.S. PATENT DOCUMENTS

| | | | |
|---|---|---|---|
| 5,388,044 A | * | 2/1995 | Hepp ................... E21B 47/026 367/25 |
| 5,838,634 A | | 11/1998 | Jones et al. |
| 7,363,158 B2 | | 4/2008 | Stelting et al. |
| 2002/0120429 A1 | | 8/2002 | Ortoleva |
| 2007/0061079 A1 | | 3/2007 | Hu |

(Continued)

FOREIGN PATENT DOCUMENTS

WO 2015/148666 10/2015

OTHER PUBLICATIONS

Enge, H et al. "From outcrop to reservoir simulation model: Workflow and procedures." Geosphere, Dec. 2007, v.3, No. 6, p. 469-490 [retrieved on May 1, 2017]. Retreived from STIC.*

(Continued)

*Primary Examiner* — Rehana Perveen
*Assistant Examiner* — Alfred H B Wechselberger
(74) *Attorney, Agent, or Firm* — Fish & Richardson P.C.

(57) ABSTRACT

The present disclosure describes methods and systems, including computer-implemented methods, computer-program products, and computer systems for integration of physical reservoir rock interpretation data into reservoir formation modeling. At least one digital photograph of a rock outcrop is generated using a mobile device and the contact and boundary features associated with the at least one digital photograph are interpreted using the mobile device. A reservoir modulation trend is generated from the interpretation of the at least one digital photograph and transmitted to a three-dimensional reservoir interpretation system. A three-dimensional lithofacies model is generated using the generated reservoir modulation trend.

20 Claims, 7 Drawing Sheets

(56) References Cited

U.S. PATENT DOCUMENTS

| | | | |
|---|---|---|---|
| 2009/0164182 A1* | 6/2009 | Pedersen | G01V 11/00 703/2 |
| 2012/0239361 A1 | 9/2012 | Vargas-Guzman | |
| 2012/0296618 A1 | 11/2012 | Hocker | |
| 2013/0046524 A1 | 2/2013 | Gathogo et al. | |
| 2013/0054201 A1* | 2/2013 | Posamentier | G01V 99/005 703/2 |
| 2013/0080133 A1 | 3/2013 | Sung et al. | |
| 2013/0297272 A1 | 11/2013 | Sung et al. | |
| 2014/0081613 A1 | 3/2014 | Dommisse et al. | |
| 2014/0149041 A1 | 5/2014 | Sung et al. | |
| 2014/0372095 A1* | 12/2014 | van der Zee | E21B 43/00 703/10 |
| 2016/0146973 A1* | 5/2016 | Johnson | G01V 1/306 702/2 |

OTHER PUBLICATIONS

Nikon D100 Firmware version 2 upgrade. User instructions [online]. Nikon USA, 2014 [retreived May 4, 2017]. Retreived from <https://web.archive.org/web/20140228211739/http://www.nikonusa.com/fileuploads/firmware_upgrades/d100.html>.*

WellCAD Multiwell. Datasheet [online]. Advanced Logic Technology, 2013 [retreived on May 2, 2017]. Retreived from <https://web.archive.org/web/20140323021109/https://www.alt.lu/pdf/wellcad_multiwell.pdf>.*

"Image and fracture analysis." Well Logging Principles and Applications: Borehold Image Analysis. Apr. 11, 2008 [retreived on May 1, 2017]. Retreived from <http://www.ldeo.columbia.edu/res/div/mgg/lodos/Education/Logging/slides/Image_fracture.pdf>.*

RMS 2013 Release Notes [online]. Roxar, 2013 [retreived May 4, 2017]. Retreived from <http://petrotools.ir/downloads/release-notes/RMS2012/RMSrelnote2013.pdf>.*

WellCAD: the composite log package. Datasheet [online]. Advanced Logic Technology, 2013 [retreived on May 2, 2017]. Retreived from <https://web.archive.org/web/20131101082339/https://www.alt.lu/pdf/wellcad_brochure.pdf>.*

"FGDC Digital Cartographic Standard for Geologic Map Symbolization (PostScript Implementation)" by USGS (2006), Federal Geographic Data Committee, Doc No. FGDC-STD-013-2006 [retrieved on Feb. 20, 2018]. Retrieved from <https://pubs.usgs.gov/tm/2006/11A02/>.*

Wang et al. "The Analysis and Annotation of 3D Photorealistic Geological Outcrop Models" GeoConvention 2013: Integration [retrieved on Apr. 1, 2019]. Retrieved from <https://www.geoconvention.com/archives/2013/436_GC2013_The_Analysis_and_Annotation.pdf> (Year: 2013).*

Arbues et al. "A Method for Producing Photorealistic Digital Outcrop Models" D029, 74th EAGE Conference and Exhibition, Copenhagen [retrieved on Apr. 18, 2019]. Retrieved from <https://www.researchgate.net/publication/259051744_A_Method_for_Producing_Photorealistic_Digital_Outcrop_Models> (Year: 2012).*

Hodgetts et al. "Laser scanning and digital outcrop geology in the petroleum industry: A review" Marine and Petroleum Geology, vol. 46, pp. 335-354 [retrieved on Apr. 22, 2019]. Retrieved from <https://www.sciencedirect.com/science/article/pii/S0264817213000494> (Year: 2013).*

Jones et al. "Extending Digital Outcrop Geology into the Subsurface" Outcrops Revitalized: Tools, Techniques and Apps, SEPM Special Publication No. 00 [retrieved on Apr. 22, 2019]. Retrieved from <https://www.researchgate.net/publication/265260888_Extending_Digital_Outcrop_Geology_into_the_Subsurface> (Year: 2010).*

Rarity et al. "LiDAR-based digital outcrops for sedimentological . . . " Geolog Soc, London, Spec Pubs, vol. 387, pp. 153-183 [retrieved on Apr. 22, 2019]. Retrieved from <https://www.researchgate.net/publication/263889499_LiDAR-based_digital_outcrops_for_sedimentological_analysis_Workflows_and_techniques> (Year: 2014).*

Hennings et al. "Combining Outcrop Data and Three-Dimensional . . . " AAPG Bull, Jun [retrieved on Apr. 22, 2019]. Retrieved from <https://www.researchgate.net/publication/277744914_Combining_Outcrop_Data_and_Three-Dinnensional_Structural_Models_to_Characterize_Fractured_Reservoirs_An_Example_from_Wyoming> (Year: 2000).*

Adams et al. "Improving reserv . . . " Petrol Geosci, vol. 17, pp. 309-332 [retrieved Apr. 22, 2019]. Retrieved <https://www.researchgate.net/publication/261588006_Improving_reservoir_models_of_Cretaceous_carbonates_with_digital_outcrop_modelling-Jabal_Madmar_Oman_Static_modelling_and_simulating_clinoforms> (Year: 2011).*

Li et al. "Textural and knowledge-based lithological classification of remote sensing data . . . " Journal of African Earth Sciences, vol. 60, pp. 237-246 [retrieved on Jul. 23, 2019]. Retrieved from <https://www.sciencedirect.com/science/article/pii/S1464343X11000586> (Year: 2011).*

Hodgetts, D. "Laser scanning and digital outcrop geology in the petroleum Industry: A review" Marine and Petroleum Geology, vol. 46, pp. 335-354 [retrieved on Jul. 23, 2019]. Retrieved from <https://www.sciencedirect.com/science/article/pii/S0264817213000494> (Year: 2013).*

Rarity et al. "LiDAR-based digital outcrops . . . " Geolog. Soc., London, Spec. Pubs., vol. 387, pp. 153-183 [retrieved on Jul. 23, 2019]. Retrieved from <https://www.researchgate.net/publication/263889499_LiDAR-based_digital_outcrops_for_sedimentological_analysis_Workflows_and_techniques> (Year: 2014).*

Jones et al. "Extending Digital Outcrop Geology into the Subsurface" doi:10.2110/sepmcsp.10.031 [retrieved on Jul. 23, 2019]. Retrieved from <https://www.researchgate.net/publication/265260888_Extending_Digital_Outcrop_Geology_into_the_Subsurface> (Year: 2011).*

Donatis et al. "Earth and Environmental Sciences: field classes with GIS/GPS and tablet" First International Workshop on Pen-Based Learning Technologies [retrieved on Dec. 16, 2019]. Retrieved from <https://ieeexplore.ieee.org/document/4488877> (Year: 2007).*

Hurley et al. "Multiscale Workflow for Reservoir Simulation" SPWLA 53rd Annual Logging Symposium, pp. 1-15 [retrieved on Dec. 13, 2019]. Retrieved from <https://www.onepetro.org/conference-paper/SPWLA-2012-195> (Year: 2012).*

Clark, J. "Detailed section across the Ainsa n Channel complex, south central Pyrenees, Spain" in [Eds. Pickering et al.] Atlas of Deep Water Environments: . . . , ISBN: 0 412 56110 7 [retrieved on Apr. 7, 2020]. Retrieved from <https://link.springer.com/content/pdf/10.1007/978-94-011-1234-5_21.pdf> (Year: 1995).*

McCaffrey et al. "Unlocking the spatial dimension: digital technologies and the future of geoscience fieldwork" Journal of the Geological Society, London, vol. 162, pp. 927-938 [retrieved on Mar. 18, 2020]. Retrieved from <https://jgs.lyellcollection.org/content/162/6/927> (Year: 2005).*

Jones et al. "Integration of regional to outcrop digital data: 3D visualization of multi-scale geological models" Computers and Geosciences, vol. 35, pp. 4-18 [retrieved on Apr. 22, 2019]. Retrieved from <https://www.sciencedirect.com/science/article/pii/S0098300407001537> (Year: 2009).*

Larue, D. "Outcrop and waterflood simulation modeling of the 100-Foot Channel Complex, Texas, and the . . . " in AAPG Memoir 80, p. 337-364 [retrieved on Apr. 7, 2020]. Retrieved from <https://pubs.geoscienceworld.org/books/book/1285/chapter/107133431/Outcrop-and-Waterflood-Simulation-Modeling-of-the> (Year: 2004).*

International Search Report and Written Opinion of the International Searching Authority issued in International Application No. PCT/US2015/056354 dated Feb. 17, 2016; 13 pages.

Wang, Miao et al.; "The Analysis and Annotation of 3D Photorealistic Geological Outcrop Models"; GeoConvention Integration; May 1, 2013; pp. 1-8.

Norris, R.J. et al.; "The Geological Modeling of Effective Permeability in Complex Heterolithic Facies"; Proceedings of SPE Annual Technical Conference and Exhibition; Jan. 1, 1991; pp. 359-374.

Hodgson et al.; "Distribution and Origin of Hybrid Beds in Sand-Rich Submarine Fans of the Tangua Depocentre, Karoo Basin, South Africa"; Marine and Petroleum Geology, vol. 26, No. 10; Dec. 1, 2009; pp. 1940-1956.

(56) References Cited

OTHER PUBLICATIONS

Gulf Coop Council Examination Report issued in GC Application No. 2015-30567 dated Apr. 8, 2018, 4 pages.

* cited by examiner

PHYSICAL RESERVOIR ROCK INTERPRETATION IN A 3D PETROPHYSICAL MODELING ENVIRONMENT

BACKGROUND

Several techniques exist to find and/or analyze subsurface reservoirs of hydrocarbons, natural gas, water, and/or other substances. For example, seismic data from sonic wave reflections can be used to indirectly estimate reservoir formation structure characteristics. As another example, a retrieved well core is a sample of a reservoir formation extracted from beneath the surface of the earth, and can provide direct/accurate measurements of reservoir formation characteristics and physical evidence related to the reservoir formation. In some cases, evidence of reservoir formation characteristics can also be found above the surface of the earth, such as that evidenced by a rock outcrop. Therefore, analyzing and characterizing rock outcrops can also provide useful information about a reservoir formation.

SUMMARY

The present disclosure describes methods and systems, including computer-implemented methods, computer-program products, and computer systems, for integration of physical reservoir rock interpretation data into reservoir formation modeling. At least one digital photograph of a rock outcrop is generated using a mobile device and the contact and boundary features associated with the at least one digital photograph are interpreted using the mobile device. A reservoir modulation trend is generated from the interpretation of the at least one digital photograph and transmitted to a three-dimensional reservoir interpretation system. A three-dimensional lithofacies model is generated using the generated reservoir modulation trend.

One computer-implemented method includes generating at least one digital photograph of a rock outcrop using a mobile device; interpreting, using the mobile device, contact and boundary features associated with the at least one digital photograph; generating a reservoir modulation trend from the interpretation of the at least one digital photograph; transmitting the generated reservoir modulation trend to a three-dimensional reservoir interpretation system; and generating a three-dimensional lithofacies model using the generated reservoir modulation trend.

Other implementations of this aspect include corresponding computer systems, apparatuses, and computer programs recorded on one or more computer-readable media/storage devices, each configured to perform the actions of the methods. A system of one or more computers can be configured to perform particular operations or actions by virtue of having software, firmware, hardware, or a combination of software, firmware, or hardware installed on the system that in operation causes or causes the system to perform the actions. One or more computer programs can be configured to perform particular operations or actions by virtue of including instructions that, when executed by data processing apparatus, cause the apparatus to perform the actions.

The foregoing and other implementations can each optionally include one or more of the following features, alone or in combination:

A first aspect, combinable with the general implementation, comprising receiving at least one well core image with the mobile device.

A second aspect, combinable with any of the previous aspects, comprising interpreting the received at least one well core image using an application executing on the mobile device.

A third aspect, combinable with the general implementation, comprising garnering a digital well core representation from the at least one well core image.

A fourth aspect, combinable with any of the previous aspects, comprising generating a well core correlation from a plurality of digital well core interpretations.

A fifth aspect, combinable with the general implementation, comprising transmitting the well core correlation to the three-dimensional reservoir interpretation system.

A sixth aspect, combinable with any of the previous aspects, wherein the well core correlation is used with the generated reservoir modulation trend to generate the three-dimensional lithofacies model.

The subject matter described in this specification can be implemented in particular implementations so as to realize one or more of the following advantages. First, data from a rock outcrop can be used to provide additional data to increase accuracy of lithofacies modeling of reservoir formations. Second, the ergonomics of the technique described in this disclosure may be similar to that of using pencil and paper, but resultant interpretive digital output can be fully integrated with geology, petrophysics, and modeling environments. The flexibility and agility of mobile interpretation directly on the field while witnessing rock formation adds substantial accuracy. Third, a 3D petrophysical model application system can use interpreted rock outcrop data to more accurately estimate reservoir formation trends between well locations. Fourth, characterization of well cores can be standardized using a uniform library of symbols, patterns, and sedimentary structures that enable a common interpretive environment and aids in correlation and analysis. Other advantages will be apparent to those of ordinary skill in the art. Fifth, integration of core lithofacies at well locations and outcrop reservoir trends between wells creates a geologically realistic formation distribution.

The details of one or more implementations of the subject matter of this specification are set forth in the accompanying drawings and the description below. Other features, aspects, and advantages of the subject matter will become apparent from the description, the drawings, and the claims.

DESCRIPTION OF DRAWINGS

Like reference numbers and designations in the various drawings indicate like elements.

DETAILED DESCRIPTION

Figure 1:
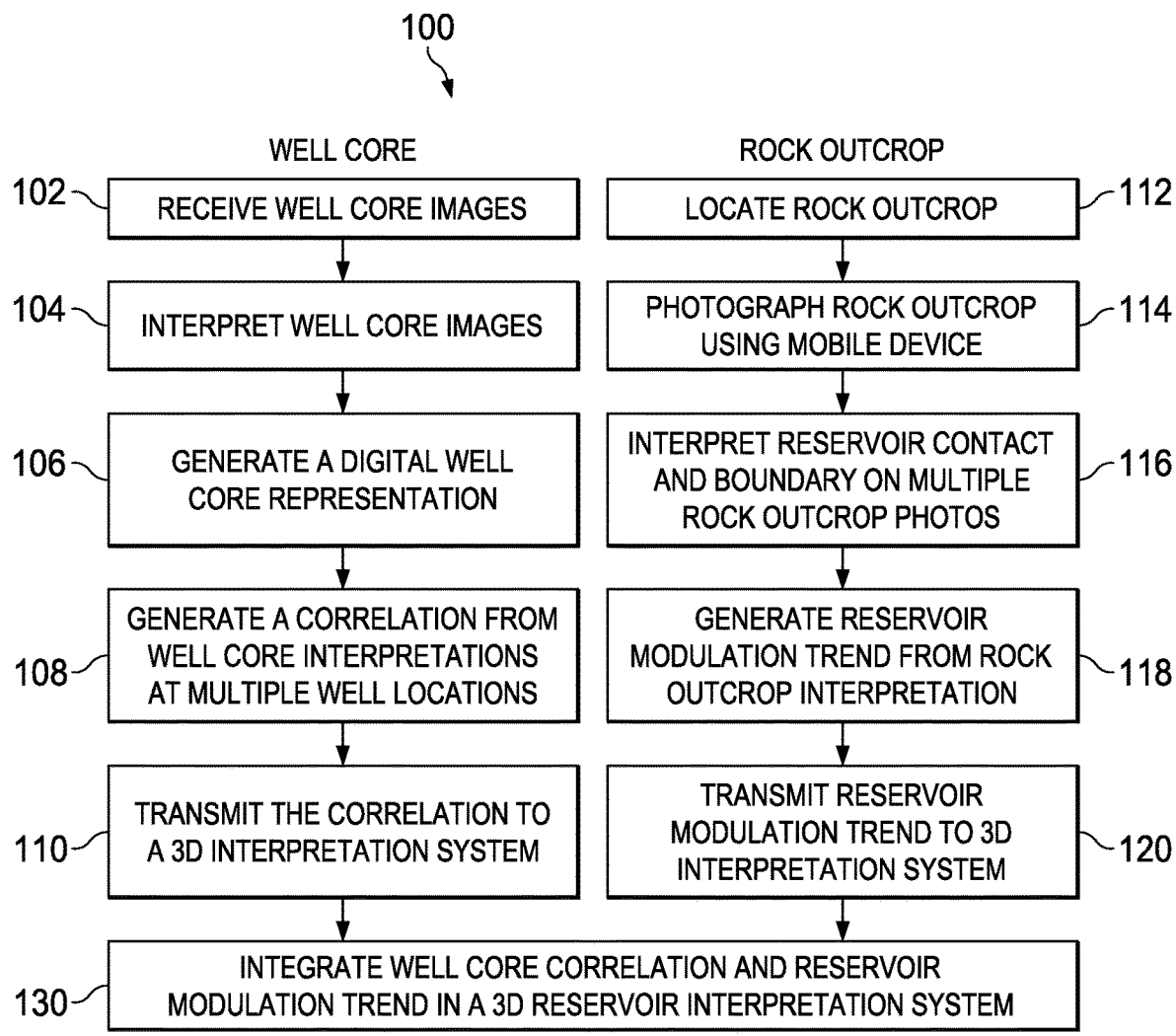
FIG. 1 illustrates a method for integration of physical reservoir rock interpretation data into reservoir formation modeling according to an implementation.

This disclosure generally describes methods and systems, including computer-implemented methods, computer-program products, and computer systems, for integration of physical reservoir rock interpretation data into reservoir formation modeling.

The following description is presented to enable any person skilled in the art to make and use the invention, and is provided in the context of one or more particular implementations. Various modifications to the disclosed implementations will be readily apparent to those skilled in the art, and the general principles defined herein may be applied to other implementations and applications without departing from scope of the disclosure. Thus, the present disclosure is not intended to be limited to the described and/or illustrated implementations, but is to be accorded the widest scope consistent with the principles and features disclosed herein.

A well core sample is a piece of rock including one or more lithofacies extracted from a wellbore beneath the earth's surface that provides actual/accurate physical evidence of reservoir formation characteristics (e.g., rock type, formation thickness, etc.). In some instances, well core samples can also reveal structural dip, fault, fracture, porosity, mineral composition, and/or other values, conditions, etc. Traditionally, geologists or other experts visually examine a well core sample and describe it on paper or in other formats. In some cases, reservoir formations can be found above the earth's surface, such as in a rock outcrop. The characteristics of rock outcrops and other surface features can be interpreted to estimate reservoir characteristics, such as the contact and boundary of a reservoir.

In many cases, multiple physical well core samples can be used to predict lithofacies and reservoir trends. For example, the data from the well core samples can interpolated to generate a 3D estimate of the reservoir by petrophysical interpretation application systems, 3D lithofacies models of reservoir formations, and lithofacies distributions by 3D petrophysical modeling application systems. However, due the 1D nature of well cores, the reservoir trend between the wells must be estimated from the well core data. Estimation/assumption of data such as inter-well trends can result in less-than-accurate lithofacies interpretations. Inaccurate results can result wasted time, needless expenditure of business resources, and/or lost business opportunity and/or revenue.

Furthermore, well cores and rock outcrops are often described by a geologist using pencil and paper or other analog techniques. Assimilation of these descriptions and interpretations into a digital workflow can involve a time consuming process of digitization, scanning, data entry, and/or quality control which is prone to human error. Without a method to quantify the earth surface characteristics, digitize those characteristics, and/or incorporate the analog data, the well and rock outcrop data is of limited use for a 3D model.

At a high level, this disclosure is drawn to integrating data from multiple well cores at well locations and reservoir trends between wells from rock outcrops in a 3D interpretation environment for modeling of reservoir formations and lithofacies distribution. The disclosure discusses enabling digital outputs from both well core interpretations and rock outcrop interpretations. Both the well core interpretation and the rock outcrop interpretation can be accomplished using a mobile or other device. For example, the mobile device can be a tablet computer, smartphone, and/or other mobile devices; other devices can include a workstation and/or a desktop computer. Use of a mobile device has similar benefits to "pen-and-paper" input such as accuracy, speed, flexibility, and portability. However, the use of a mobile device has the additional benefits of input digitization and standardization.

Using the mobile device, the description and information interpreted from a well core and/or rock outcrop can be entered on a touch-sensitive device using a finger, stylus, and/or other implement. For example, geoscientists can use a mobile device to describe physical well cores while walking around a well core storage facility or at later time/place. Geoscientists can also use a mobile device to describe a rock outcrop after taking a rock outcrop digital photograph while in the area of the rock outcrop or at a later time/place.

The mobile device can display information (e.g., well core characteristics, rock outcrop characteristics, and/or other information) on a portable screen, which can facilitate on-site interpretation and identification of a well core and/or rock outcrop. In some implementations, interpretations of a well core and/or rock outcrop can be performed by selecting from a uniform library of symbols, patterns, characteristics, and/or sedimentary structures and using standardized reservoir-type templates. This standardization enables a common interpretive environment for well cores and rock outcrops that aids correlation and analysis using digital photographs, even when using interpretations from multiple geoscientists.

The mobile device can take digital photographs of a rock outcrop with Global Position System (GPS) coordinates and/or other location data (e.g., manually entered landmarks, etc.). The use of multiple digital photographs with geographic coordinates (e.g., a panoramic image) can also create an area-type sense of a rock outcrop formation(s) and provide further 3D interpretive context. Picking reservoir boundaries based on well core and/or rock outcrop observation details, for example, geographic strata, color differences, depth, composition, etc. on the photographs can also yield valuable reservoir trends.

This digital well core and digital rock outcrop interpretive information can be digitized and integrated into a 3D interpretation environment. The well core information can provide 1D hard data at specific well locations, and the rock outcrop information can provide soft data of reservoir trends at locations between the well locations. By incorporating both the well core and the rock outcrop data into an integrated 3D digital interpretation, the accuracy of a 3D interpretation of a particular reservoir can be substantially improved.

FIG. 1 illustrates a method 100 for integration of physical reservoir rock interpretation data into reservoir formation modeling according to an implementation. For clarity of presentation, the description that follows generally describes method 100 in the context of FIGS. 2-3, 4A-4B, and 5-7. Method 100 may be performed by any suitable system, environment, software, and/or hardware, or a combination of systems, environments, software, and/or hardware as appropriate (e.g., the computer system described in FIG. 7 below). In some implementations, various steps of method 100 can be run in parallel, in combination, in loops, or in any order. The portions of example method 100 that substantially concern well core interpretation are 102, 104, 106, 108, and 110. The portions of example method 100 that substantially concern rock outcrop interpretation are 112, 114, 116, 118, and 120. 130 combines both well core and rock outcrop interpretation data in a 3D reservoir interpretation system.

Well Core Data

At 102, a well core physical rock or image is received. For example, a mobile device can receive a well core image (e.g., a digital photograph) from a camera included in the mobile device. In some implementations, the mobile device can be a tablet computer, smartphone, or other mobile device. For example, the mobile device can be a device like mobile device 740 in FIG. 7 that is described below. In some implementations, a well core image can be obtained or generated from a separate system or device (e.g., another mobile device) and transmitted/made available to the mobile device (e.g., over a network). In some implementations, multiple well core images are received. In some implementations, multiple well core images can be combined into a single image either by the mobile device or a separate system or device prior to receipt by the mobile device. From 102, method 100 proceeds to 104.

At 104, the well core images are interpreted. For example, the well core images can be interpreted by a geoscientist. The interpretation of the well core can include characteristics of the well core, such as measured depth, Dunham texture, mineral composition, porosity, major and minor grain size, biostratigraphic information (e.g., fossil type and density), classification, structure, or other characteristics. The interpretation of the well core can be displayed on computer such as the above-described mobile device, a workstation, and/or other computing device.

Figure 2:
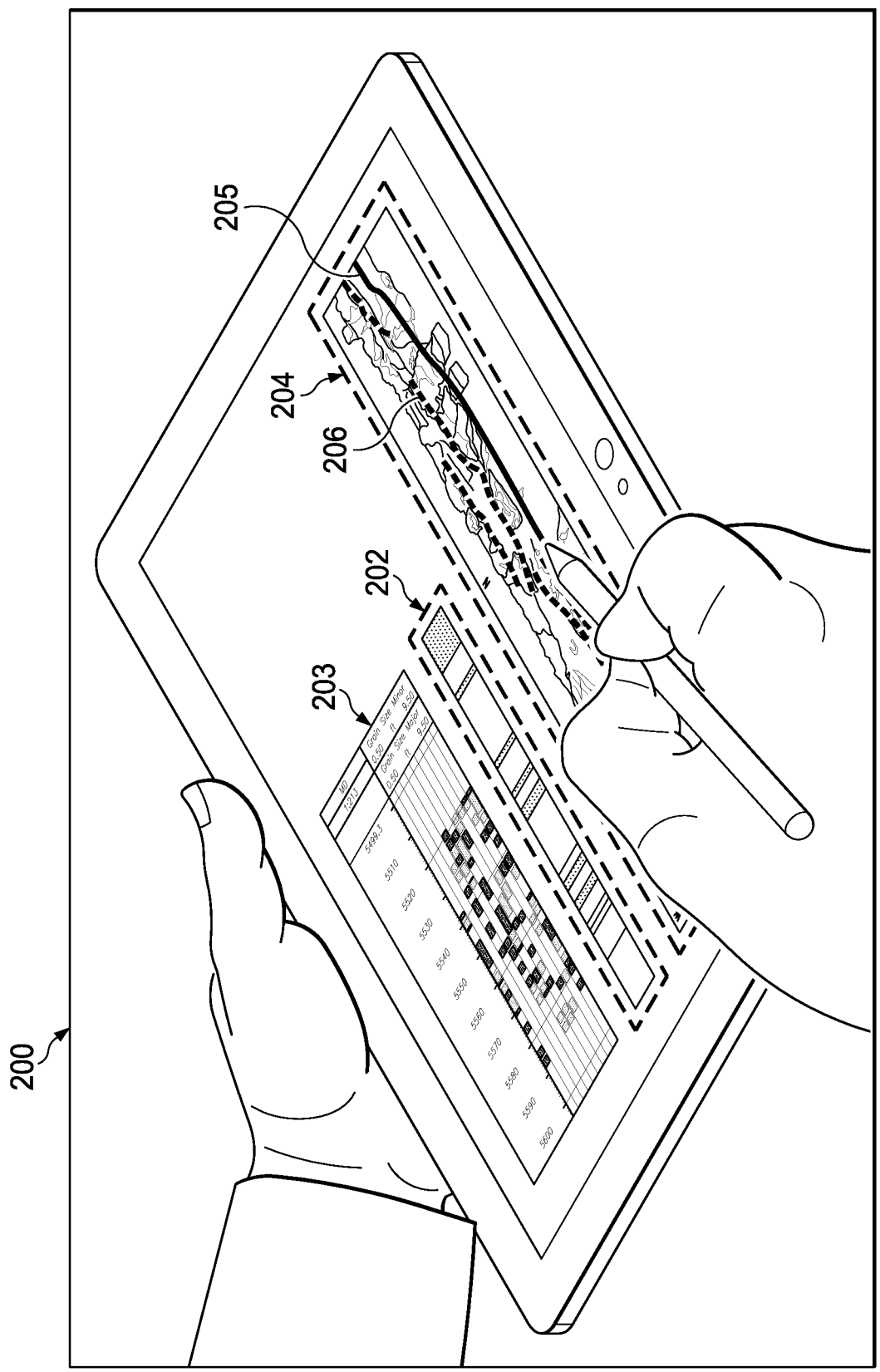
FIG. 2 illustrates an implementation of an example mobile device for core and rock outcrop characterization according to an implementation.

Referring to FIG. 2, FIG. 2 illustrates an implementation of an example mobile device 200 for well core and rock outcrop characterization according to an implementation. A mobile device user can digitally interpret images of well cores 202 in a manner similar to interpreting rock outcrop data (see 204 and FIGS. 1 and 4A/4B). For example, the mobile device 200 can display one or more well core images 202 and the images can be interpreted (e.g., using lines, symbols, text, etc.) using a touch-sensitive screen on mobile device 200 to produce/display on the mobile device well core interpretive data 203.

The interpreted well core data 203 is a digital representation of a performed well core image 202 interpretation. For example, touching a touch-sensitive screen can mark well core image data 202 with strata, color, composition, etc. information. Interpreted well core data 203 can, in some instances, dynamically change to reflect entered interpretive criteria. In some implementations, a well core interpretation can be performed by selecting from a set of standardized interpretation templates, characteristics, and/or from a set of characteristic values.

Figure 3:
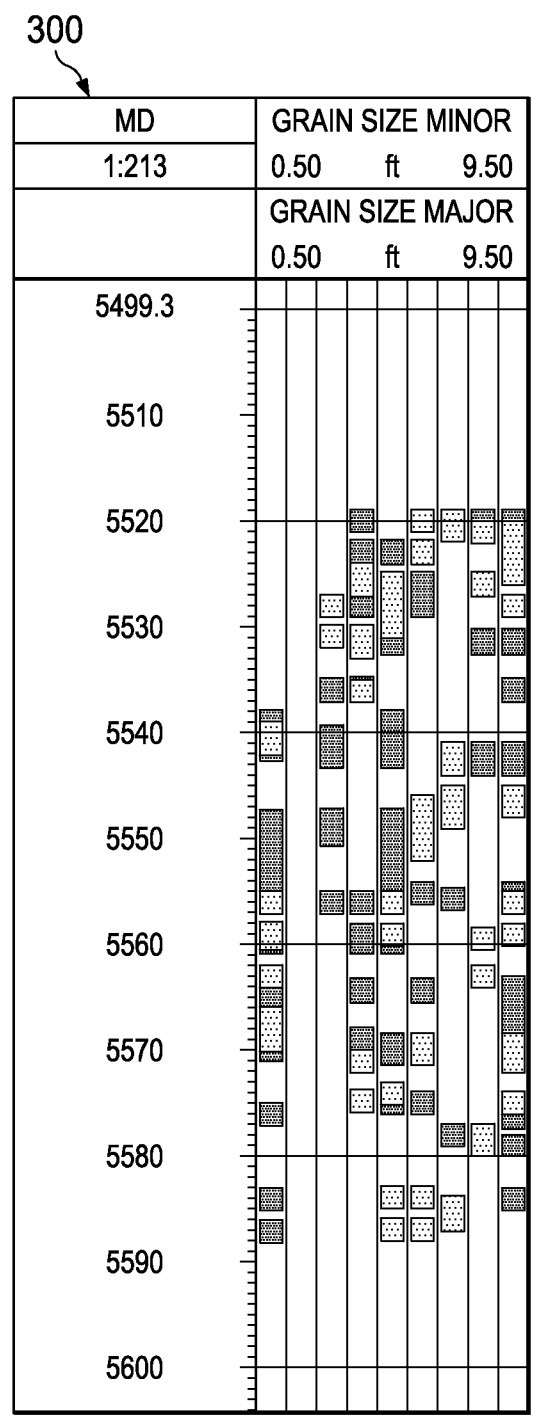
FIG. 3 illustrates an example well core interpretation according to an implementation.

Referring to FIG. 3, FIG. 3 illustrates an example well core interpretation 300 (e.g., similar to interpreted well core data 203 in FIG. 2) according to an implementation. The example well core interpretation 300 can be displayed as interpreted well core data 203. The example well core interpretation 300 shows major grain and minor grain histogram for a portion of a well core. This shows the grain size distribution in the core leading to indication of the depositional environment. Other interpretations can show different aspect of the core characteristics, as described previously and including, for example, biostratigraphic fossil occurrence, Dunham texture, etc.

Returning to FIG. 1, from 104, method 100 proceeds to 106. At 106, a digital well core representation is generated. A digital well core representation is created from a digital collection (e.g., from mobile/computing devices of one or more interpreters) of well core interpretation(s), characteristics, and other information (e.g., well location, well azimuth, well inclination, etc.) for a particular well core. For example, a digital well core representation of a well core can be generated, in part, from one or more interpretations of the well core. In the case of multiple interpretations, the interpretive data can be processed to produce a correlated interpretation. A digital well core representation can be generated for each well core in a set of well locations. From 106, method 100 proceeds to 108.

At 108, a correlation is generated from well core interpretations at multiple well locations. For example, digital well core representations can be correlated and interpolated to estimate an overall reservoir sequence stratigraphy trend. From 108, method 100 proceeds to 110.

At 110, the correlation is transmitted to a 3D interpretation system for integration into a modeling environment. From 110, method 100 proceeds to 130.

At 130, the well core correlation is integrated/combined with a generated reservoir modulation trend (see below) into the 3D interpretation system to further analyze the different data objects (i.e., well core correlation and reservoir modulation trend) to make a better subsurface reservoir prediction. Well core interpretation (110), while very accurate vertically, is limited by the generally few wells (tens) drilled in a reservoir field. A reservoir modulation trend interpreted from rock outcrops (120) provides a much better lateral resolution between wells. At 130, not only digital lithofacies from well cores and reservoir trends from rock outcrops are integrated, but also the accurate lithofacies interpreted at well locations can be guided by reservoir trends between wells to form an accurate 3D lithofacies model. From 130, method 100 stops.

Rock Outcrop Data

Figure 4A:
FIGS. 4A-B illustrate an example rock outcrop digital photograph and the photograph with reservoir contact and boundary interpretive notations according to an implementation.
Figure 4B:
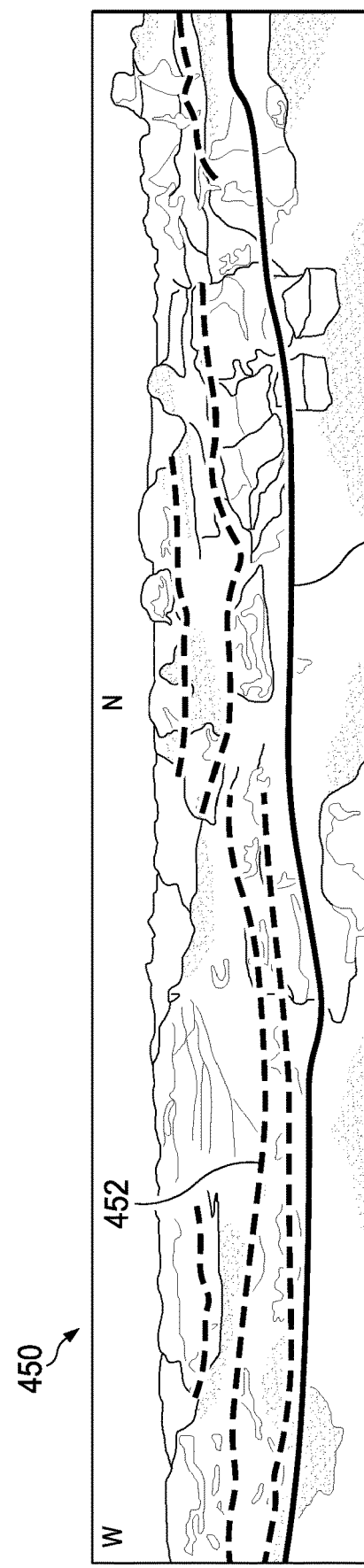

FIGS. 4A-4B illustrate an example rock outcrop digital photograph 400 and the photograph 450 with reservoir contact and boundary interpretive notations according to an implementation. For example, FIG. 4A can represent a rock outcrop discovered by a geoscientist at a particular geographic location associated with a set of well locations.

Turning to the portions of method 100 that describe rock outcrop interpretation, at 112, a rock outcrop is located on the earth's surface. From 112, method 100 proceeds to 114.

At 114, one or more photographs of the rock outcrop are taken. The photographs can be digital photographs taken with a mobile device such as mobile device 200, mobile device 740, and/or another mobile device as described previously. In some implementations, photographs can be taken with one device and transferred to another device or system. In some implementations, information about the photograph (e.g., GPS surface coordinates of the photographed location, time and date the photograph was taken, user-entered information (e.g., text, descriptive marks, etc.), dynamically associated information, etc.) can be stored in image headers, metadata, etc. and/or be stored separately and associated with the image. From 114, method 100 proceeds to 116.

At 116, the photographs are interpreted to determine rock outcrop characteristics. For example, rock outcrop features such as rock outcrop color changes, rock outcrop composition changes, rock outcrop texture changes, rock outcrop contrast, reservoir contacts, reservoir boundaries, and/or other features can be identified and designated on each digital photograph. In some implementations, the rock outcrop digital photographs can be displayed on a mobile device, workstation, or other computing device. A geoscientist can identify rock outcrop features on the photographs and digitally designate the locations and characteristics of the rock outcrop features on the digital photographs. For example, lines or curves representing observed reservoir boundaries (or other interpretations) can be digitally designated on the displayed digital photographs using a touch-sensitive screen, stylus, etc.

Referring to FIG. 2, a digital photograph 204 can be displayed on mobile device 200, and the user can designate multiple rock outcrop features associated with different formations on the digital photograph 204 using the touch-sensitive screen of the mobile device 200 (e.g., lines 205 and 206). In some implementations, in addition to the digital photograph 204, the mobile device 200 can also show information such as well core images 202, well core interpretive data 203, other digital photographs, or other information. Showing other information in addition to digital photograph 204 and associated interpretive markups to digital photograph 204 can assist in interpretation and analysis of the digital photograph 204 by providing contextual data. For example, well core image data 202 can be correlated to observed rock outcrop features displayed in digital photograph 204 to allow a more accurate interpretation of those features. From 116, method 100 proceeds to 118.

Referring to FIG. 4B, FIG. 4B shows an example interpreted rock outcrop image 450. Interpreted image 450 includes digital photograph 400 (e.g., digital photograph 204) and example interpretive notations 452 and 454. The interpretive notations 452 and 454 are the locations of observed rock outcrop features. For example, notation 452 can be a curve representing a location of a first reservoir contact/boundary, and notation 454 can be a curve representing the location of a second contact/reservoir boundary. Multiple notations can be made on the digital photograph 400. Each notation can have different properties (e.g., line color, line thickness, annotations, etc.) to represent individual notations, certain types of notations (e.g., boundary, contact, reservoir type, etc.), and/or certain characteristics of a particular feature(s) (e.g., color, composition, etc.). The properties of a notation can be modified during image interpretation. In some implementations, each notation can be associated with a well core. In some implementations, notations on multiple photographs can be associated, for example, if the notations represent the same reservoir contact feature spanning multiple digital photographs. In some implementations, the actual surface location of a noted feature can be generated from one or more photographs and associated information (e.g., GPS coordinates, elevation, spatial measurements, optical properties of the camera, etc.). The actual location of a notation can include a set of geospatial coordinates.

Returning to FIG. 1, at 118, a reservoir modulation trend is generated from the rock outcrop interpretation. The reservoir modulation trend can be generated from the digital notations at 116. For example, interpretation data (i.e., notations) can result in X and Y coordinates and Z coordinates associated with noted contact and/or boundary lines associated with a rock outcrop. In some implementations, data associated with one or more photographs and/or multiple rock outcrops can be combined (if applicable) and used to generate a reservoir modulation trend. For example, notations and associated location information can be interpolated to generate an estimate of horizontal reservoir trend. In this manner, reservoir trends can be estimated in inter-well regions. From 118, method 100 proceeds to 120.

At 120, the generated reservoir modulation trend is transmitted to the 3D interpretation system for integration into a modeling environment. From 120, method 100 proceeds to 130.

Figure 5:
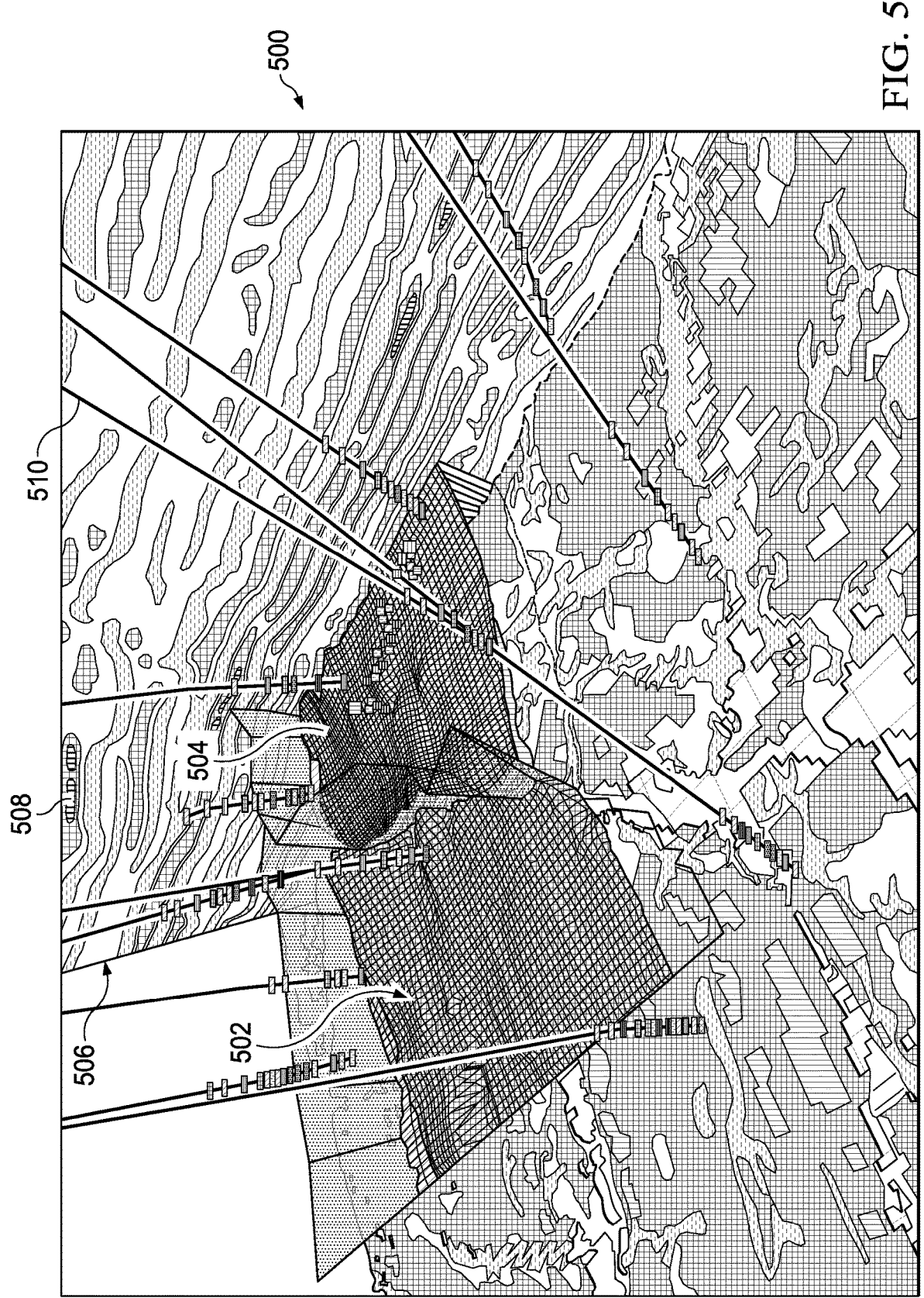
FIG. 5 illustrates an example of a 3D interpretation that incorporates core lithofacies description and rock outcrop contact and boundary interpretation according to an implementation.
Figure 6:
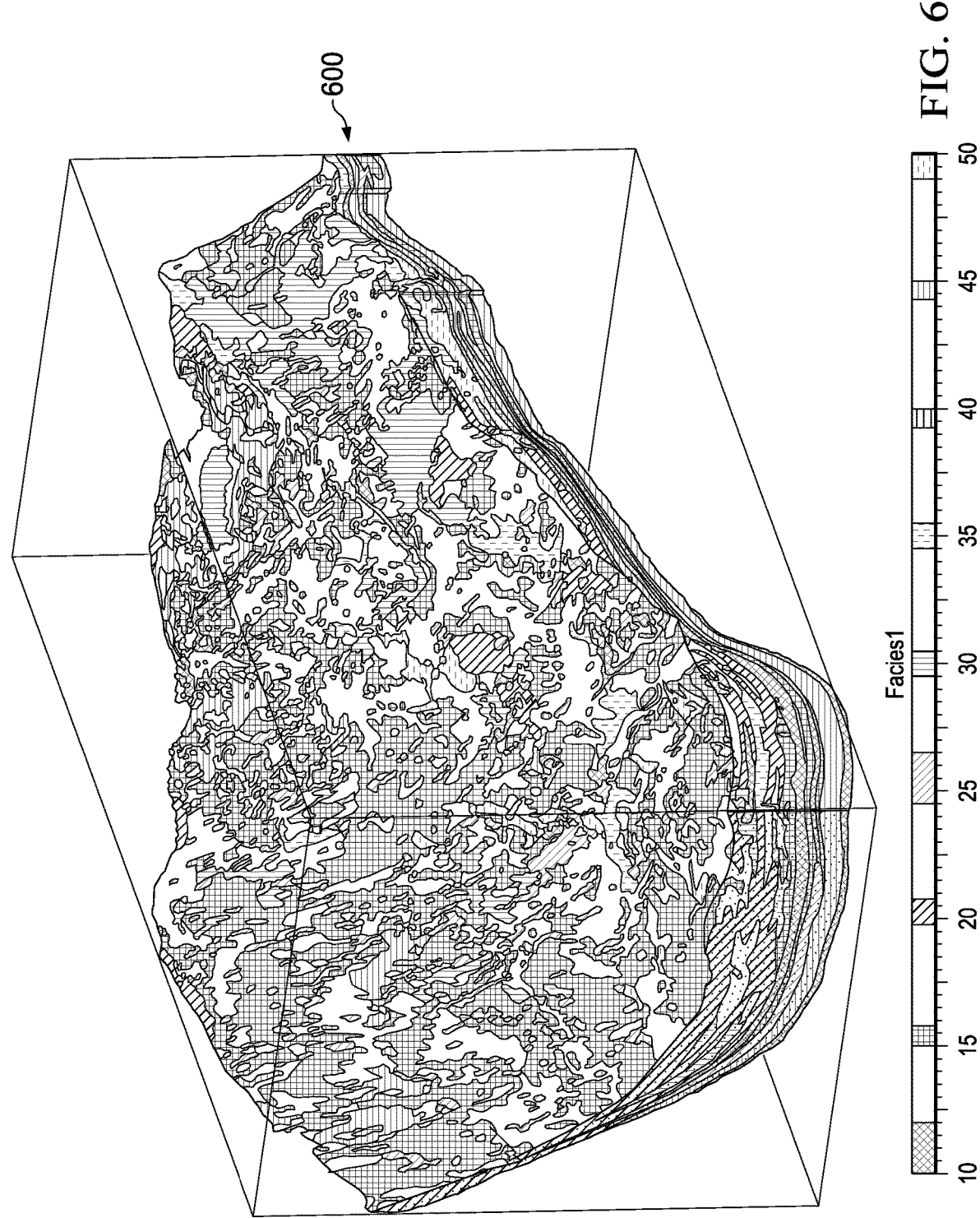
FIG. 6 illustrates an example 3D geological model highlighting lithofacies distribution according to an implementation.

At 130, the generated well core correlation and the reservoir modulation trend are integrated into a 3D interpretation system. For example, the 3D interpretation system can be a reservoir model implemented by a computing system such as a computer or distributed computer system, such as the system shown below in FIG. 7. In some implementations, the reservoir modulation trend is integrated into the well core correlation to generate a lithofacies 3D model. The well core correlation can represent hard reservoir data, and the reservoir modulation trend can represent soft reservoir data to estimate inter-well regions and horizontal trends. For example, FIG. 5 illustrates an example of a 3D interpretation 500 that incorporates well core lithofacies description and rock outcrop contact and boundary interpretation according to an implementation. FIG. 5 includes multiple wells (one designated by well trajectory 510) that each include well core interpretation data (e.g., well core interpretation data 203). The well core interpretation data can be represented by symbols, colors, and/or other indications on each well trajectory. The model 500 also includes an example reservoir trend 502 that is generated from the reservoir modulation trend and the well core correlation. A denser reservoir trend surface 504 can be interpolated and generated from reservoir trend lines interpretation from multiple outcrop photographs. These surfaces form the framework of 3D lithofacies modeling. The 3D interpretation system can also incorporate other types of data from other sources. For example, the model 500 includes seismic data 506 that can indicate one or more possible reservoir locations (e.g., location 508) as estimated from the seismic data. As another example, FIG. 6 illustrates an example 3D geological model 600 highlighting lithofacies distribution according to an implementation.

Figure 7:
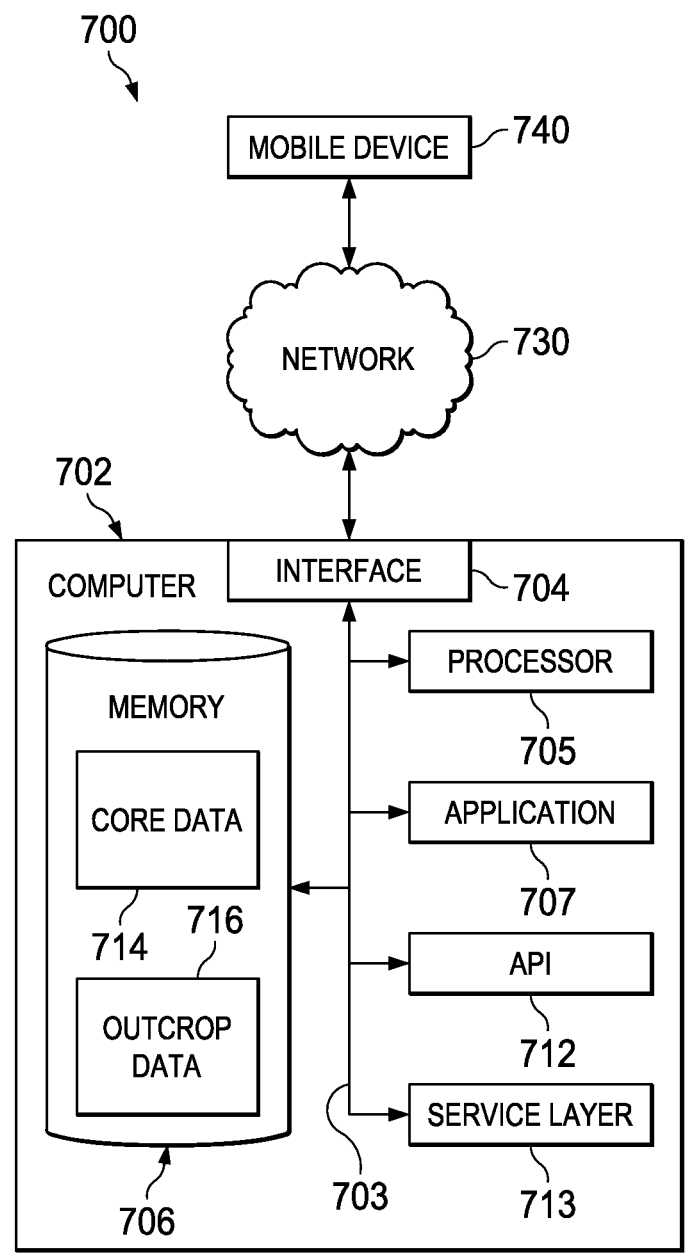
FIG. 7 is a block diagram illustrating an exemplary distributed computer system (EDCS) used to integrate physical reservoir rock interpretation data into reservoir formation modeling according to an implementation.

Turning to FIG. 7, FIG. 7 is a block diagram illustrating an exemplary distributed computer system (EDCS) 700 used to integrate physical reservoir rock interpretation data into reservoir formation modeling according to an implementation. In some implementations, the EDCS 700 includes a computer 702, network 730, and mobile device 740. In some implementations, the mobile device 740 is included as part of computer 702. In some cases, mobile device 740 is a computer including some or all of the same features as computer 702 described below.

The illustrated computer 702 is intended to encompass a computing device such as a server, desktop computer, tablet, laptop/notebook computer, wireless data port, smart phone, personal data assistant (PDA), tablet computing device, one or more processors within these devices, or any other suitable processing device, including both physical and/or virtual instances of the computing device. The computer 702 may comprise a computer that includes an input device, such as a keypad, keyboard, touch screen, or other device (not illustrated) that can accept user information, and an output device (not illustrated) that conveys information associated with the operation of the computer 702, including digital data, visual and/or audio information, or a user interface.

The computer 702 can serve as a client (e.g., a mobile device) and/or a server (e.g., a workstation and/or a super-computing node). In typical implementations, the computer 702 acts as either a mobile device (e.g., mobile device 200), a parallel processing node, a host for a software agent, and/or a host for an executing application 707 (e.g., simulation, simulator, library function, system administration, and/or other application 707) consistent with this disclosure (even if not illustrated). The illustrated computer 702 is communicably coupled with a network 730. In some implementations, one or more components of the computer 702 may be configured to operate within a parallel-processing and/or cloud-computing-based environment. Implementations of the computer 702 can also communicate using message passing interface (MPI) or other interface over network 730.

At a high level, the computer 702 is an electronic computing device operable to receive, transmit, process, store, or manage data and information associated with modeling of reservoir formations and lithofacies distribution. According to some implementations, the computer 702 may also include or be communicably coupled with a simulation server, application server, e-mail server, web server, caching server, streaming data server, business intelligence (BI) server, and/or other server.

The computer 702 can receive requests over network 730 from an application 707 (e.g., executing on another computer 702) and responding to the received requests by processing the said requests in an appropriate software application 707. In addition, requests may also be sent to the computer 702 from internal users (e.g., from a command console or by other appropriate access method), external or third-parties, other automated applications, as well as any other appropriate entities, individuals, systems, or computers.

Each of the components of the computer 702 can communicate using a system bus 703. In some implementations, any and/or all the components of the computer 702, both hardware and/or software, may interface with each other and/or the interface 704 over the system bus 703 using an application programming interface (API) 712 and/or a service layer 713. The API 712 may include specifications for routines, data structures, and object classes. The API 712 may be either computer-language independent or dependent and refer to a complete interface, a single function, or even a set of APIs. The service layer 713 provides software services to the computer 702 and/or system of which the computer 702 is a part. The functionality of the computer 702 may be accessible for all service consumers using this service layer. Software services, such as those provided by the service layer 713, provide reusable, defined business functionalities through a defined interface. For example, the interface may be software written in JAVA, C++, or other suitable language providing data in extensible markup language (XML) format or other suitable format. While illustrated as an integrated component of the computer 702, alternative implementations may illustrate the API 712 and/or the service layer 713 as stand-alone components in relation to other components of the computer 702. Moreover, any or all parts of the API 712 and/or the service layer 713 may be implemented as child or sub-modules of another software module, enterprise application, or hardware module without departing from the scope of this disclosure.

The computer 702 includes an interface 704. Although illustrated as a single interface 704 in FIG. 7, two or more interfaces 704 may be used according to particular needs, desires, or particular implementations of the computer 702. The interface 704 is used by the computer 702 for communicating with other systems in a distributed environment—including a parallel processing environment—connected to the network 730 (whether illustrated or not). Generally, the interface 704 comprises logic encoded in software and/or hardware in a suitable combination and operable to communicate with the network 730. More specifically, the interface 704 may comprise software supporting one or more communication protocols associated with communications over network 730.

The computer 702 includes a processor 705. Although illustrated as a single processor 705 in FIG. 7, two or more processors may be used according to particular needs, desires, or particular implementations of the computer 702. Generally, the processor 705 executes instructions and manipulates data to perform the operations of the computer 702. Specifically, the processor 705 executes the functionality required to integrate physical reservoir rock interpretation data into reservoir formation models.

The computer 702 also includes a memory 706 that holds data for the computer 702 and/or other components of a system of which the computer is a part. Although illustrated as a single memory 706 in FIG. 7, two or more memories may be used according to particular needs, desires, or particular implementations of the computer 702. While memory 706 is illustrated as an integral component of the computer 702, in alternative implementations, memory 706 can be external to the computer 702. In some implementations, memory 706 can hold and/or reference one or more of, as described above, well core data 714 or rock outcrop data 716.

The application 707 is an algorithmic software engine providing functionality according to particular needs, desires, or particular implementations of the computer 702 and/or a system of which the computer 702 is a part, particularly with respect to functionality required to integrate physical reservoir rock interpretation data into reservoir formation models. For example, application 707 can serve as (or a portion of) a simulation, simulator, parallel processing node, library function, software agent, system administrator, and/or other application consistent with this disclosure (whether illustrated or not). In some implementations, software applications can include one or more of the above-described digital photo interpretation application (e.g., for one or both of well core images and rock outcrop digital photographs), petrophysical interpretation application, and/or petrophysical modeling application. Although illustrated as a single application 707, the application 707 may be implemented as multiple applications 707 on the computer 702. In addition, although illustrated as integral to the computer 702, in alternative implementations, the application 707 can be external to and execute apart from an instance of the computer 702.

There may be any number of computers 702 associated with a computer system performing functions consistent with this disclosure. Further, the term "client," "user," and other appropriate terminology may be used interchangeably as appropriate without departing from the scope of this disclosure. Moreover, this disclosure contemplates that many users/processes may use one computer 702, or that one user/process may use multiple computers 702.

Mobile device 740 is operable to at least capture an image of a well core sample or a rock outcrop. In some implementations, mobile device 740 can use a lens assembly to focus light onto an electronic image sensor and digitally record image information into a memory (not illustrated) in various digital file formats. For example, digital file formats used to record the image information may be JPG, GIF, BMP, TIFF, PNG, AVI, DV, MPEG, MOV, WMV, RAW, or other suitable digital file format. In some implementations, the electronic image sensor can be a charge coupled device (CCD), an active pixel sensor (CMOS), or other suitable electronic image sensor. Mobile device 740 may provide a live preview of the external image source to be photographed. Mobile device 740 may also provide optical and/or digital zoom functionality and panoramic images in both two and three dimensions. In other implementations, the recorded image information can be both still and video with sound.

In some implementations, image data recorded by mobile device 740 may also be transferred over network 730 to a remote data storage location (not illustrated) instead of being stored in memory 706. Although illustrated as communicably connected (e.g., by a cable, wireless connection, etc.) through network 730 to computer 702, in some implementations, mobile device 740 may also be integrated into computer 702 and/or other component (not illustrated) of computer system 700 or directly connected to an interface port (not illustrated) on computer 702. While the computer system 700 is illustrated as containing a single mobile device 740, alternative implementations of computer system 700 may include any number of mobile devices 740, working individually or in concert, and suitable to the purposes of the EDCS 700. In some implementations, mobile device(s) 740 can be part of a mechanical assembly (not illustrated) for moving, adjusting, stabilizing, etc. the mobile device(s) 740 and/or a well core sample to obtain the image of the well core sample or rock outcrop.

Implementations of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible, non-transitory computer-storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example, a programmable processor, a computer, or multiple processors or computers. The apparatus can also be or further include special purpose logic circuitry, e.g., a central processing unit (CPU), a co-processor (e.g., a graphics/visual processing unit (GPU/VPU)), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example LINUX, UNIX, WINDOWS, MAC OS, ANDROID, IOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a CPU, a FPGA, or an ASIC.

Computers suitable for the execution of a computer program can be based on general or special purpose microprocessors, both, or any other kind of CPU. Generally, a CPU will receive instructions and data from a read-only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a global positioning system (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., erasable programmable read-only memory (EPROM), electrically-erasable programmable read-only memory (EEPROM), and flash memory devices; magnetic disks, e.g., internal hard disks or removable disks; magneto-optical disks; and CD-ROM, DVD+/−R, DVD-RAM, and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), LED (Light Emitting Diode), or plasma monitor, for displaying information to the user and a keyboard and a pointing device, e.g., a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of UI elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of wireline and/or wireless digital data communication, e.g., a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n and/or 802.20, all or a portion of the Internet, and/or any other communication system or systems at one or more locations. The network may communicate with, for example, Internet Protocol (IP) packets, Frame Relay frames, Asynchronous Transfer Mode (ATM) cells, voice, video, data, and/or other suitable information between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware and/or software, may interface with each other and/or the interface using an application programming interface (API) and/or a service layer. The API may include specifications for routines, data structures, and object classes. The API may be either computer language independent or dependent and refer to a complete interface, a single function, or even a set of APIs. The service layer provides software services to the computing system. The functionality of the various components of the computing system may be accessible for all service consumers via this service layer. Software services provide reusable, defined business functionalities through a defined interface. For example, the interface may be software written in JAVA, C++, or other suitable language providing data in extensible markup language (XML) format or other suitable format. The API and/or service layer may be an integral and/or a stand-alone component in relation to other components of the computing system. Moreover, any or all parts of the service layer may be implemented as child or sub-modules of another software module, enterprise application, or hardware module without departing from the scope of this disclosure.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation and/or integration of various system modules and components in the implementations described above should not be understood as requiring such separation and/or integration in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

What is claimed is:

1. A computer-implemented method comprising:
generating, by a mobile computing device, at least one digital photograph of each of a plurality of rock outcrops in a region for use in digital interpretation of the rock outcrop by a user while the digital photograph is displayed on the mobile computing device;
for each of the plurality of rock outcrops, generating, by the mobile computing device, a display comprising the at least one digital photograph of the rock outcrop, the display enabling a standardized user input comprising digital interpretive data associated with contact and boundary features of the rock outcrop;
for each of the plurality of rock outcrops, receiving, by the mobile computing device, the standardized user input comprising the digital interpretive data including reservoir boundaries in that rock outcrop;
for each of the plurality of rock outcrops, generating, by the mobile computing device, a respective interpreted rock outcrop image comprising interpretive notations indicating locations of observed rock outcrop features, the observed rock outcrop features comprising: rock outcrop color changes, rock outcrop composition changes, rock outcrop texture changes, rock outcrop contrast, reservoir contacts, and the reservoir boundaries;
determining, by the mobile computing device from the interpretive notations, spatial coordinates associated with a plurality of the observed rock outcrop features;
for each of the plurality of rock outcrops, storing, by the mobile computing device, the digital interpretive data in metadata of the respective interpreted rock outcrop image;
combining, by the mobile computing device, the reservoir boundaries from the plurality of outcrops to generate a reservoir modulation trend, wherein the generating comprises:
interpolating, for at least two rock outcrops of the plurality of rock outcrops, the interpretive notations for regions among the spatial coordinates associated with the plurality of the observed rock outcrop features of the at least two rock outcrops, and
estimating, based on the interpolation, modulation of the reservoir boundaries of the plurality of outcrops;
transmitting, by the mobile computing device, the generated reservoir modulation trend to a three-dimensional reservoir interpretation system;
generating, using the reservoir modulation trend, a three-dimensional lithofacies model of the region; and
drilling one or more wells based on the three-dimensional lithofacies model.

2. The method of claim 1, comprising receiving at least one well core image with the mobile computing device.

3. The method of claim 2, comprising interpreting the received at least one well core image using an application executing on the mobile computing device.

4. The method of claim 3, comprising garnering a digital well core representation from the at least one well core image.

5. The method of claim 4, comprising generating a well core correlation from a plurality of digital well core interpretations.

6. The method of claim 5, comprising transmitting the well core correlation to the three-dimensional reservoir interpretation system.

7. The method of claim 6, wherein the well core correlation is used with the generated reservoir modulation trend to generate the three-dimensional lithofacies model.

8. A non-transitory, computer-readable medium storing computer-readable instructions, the instructions executable by a computer and configured to:
generate, by a mobile computing device, at least one digital photograph of each of a plurality of rock outcrops in a region for use in digital interpretation of the rock outcrop by a user while the digital photograph is displayed on the mobile computing device;
for each of the plurality of rock outcrops, generate, by the mobile computing device, a display comprising the at least one digital photograph of the rock outcrop, the display enabling a standardized user input comprising digital interpretive data associated with contact and boundary features of the rock outcrop;
for each of the plurality of rock outcrops, receive, by the mobile computing device, the standardized user input comprising the digital interpretive data including reservoir boundaries in that rock outcrop;
for each of the plurality of rock outcrops, generate, by the mobile computing device, a respective interpreted rock outcrop image comprising interpretive notations indicating locations of observed rock outcrop features, the observed rock outcrop features comprising: rock outcrop color changes, rock outcrop composition changes, rock outcrop texture changes, rock outcrop contrast, reservoir contacts, and the reservoir boundaries;
determine, by the mobile computing device from the interpretive notations, spatial coordinates associated with a plurality of the observed rock outcrop features;
for each of the plurality of rock outcrops, store, by the mobile computing device, the digital interpretive data in metadata of the respective interpreted rock outcrop image;
combine, by the mobile computing device, reservoir boundaries from the plurality of outcrops to generate a reservoir modulation trend, wherein the generating comprises:
interpolating, for at least two rock outcrops of the plurality of rock outcrops, the interpretive notations for regions among the spatial coordinates associated with the plurality of the observed rock outcrop features of the at least two rock outcrops, and
estimating, based on the interpolation, modulation of the reservoir boundaries of the plurality of outcrops;
transmit, by the mobile computing device, the generated reservoir modulation trend to a three-dimensional reservoir interpretation system;
generate using the reservoir modulation trend, a three-dimensional lithofacies model of the region; and
drill one or more wells based on the three-dimensional lithofacies model.

9. The medium of claim 8, comprising instructions to receive at least one well core image with the mobile computing device.

10. The medium of claim 9, comprising instructions to interpret the received at least one well core image using an application executing on the mobile computing device.

11. The medium of claim 10, comprising instructions to garner a digital well core representation from the at least one well core image.

12. The medium of claim 11, comprising instructions to generate a well core correlation from a plurality of digital well core interpretations.

13. The medium of claim 12, comprising instructions to transmit the well core correlation to the three-dimensional reservoir interpretation system.

14. The medium of claim 13, wherein the well core correlation is used with the generated reservoir modulation trend to generate the three-dimensional lithofacies model.

15. A system, comprising:
a memory;
at least one hardware processor interoperably coupled with the memory and configured to:
generate, by a mobile computing device, at least one digital photograph of each of a plurality of rock outcrops in a region for use in digital interpretation of the rock outcrop by a user while the digital photograph is displayed on the mobile computing device;
for each of the plurality of rock outcrops, generate, by the mobile computing device, a display comprising the at least one digital photograph of the rock outcrop, the display enabling a standardized user input comprising digital interpretive data associated with contact and boundary features of the rock outcrop;
for each of the plurality of rock outcrops, receive, by the mobile computing device, the standardized user input comprising the digital interpretive data including reservoir boundaries in that rock outcrop;
for each of the plurality of rock outcrops, generate, by the mobile computing device, a respective interpreted rock outcrop image comprising interpretive notations indicating locations of observed rock outcrop features, the observed rock outcrop features comprising: rock outcrop color changes, rock outcrop composition changes, rock outcrop texture changes, rock outcrop contrast, reservoir contacts, and the reservoir boundaries;
determine, by the mobile computing device from the interpretive notations, spatial coordinates associated with a plurality of the observed rock outcrop features;
for each of the plurality of rock outcrops, store, by the mobile computing device, the digital interpretive data in metadata of the respective interpreted rock outcrop image;
combine, by the mobile computing device, reservoir boundaries from the plurality of outcrops to generate a reservoir modulation trend, wherein the generating comprises:
interpolating, for at least two rock outcrops of the plurality of rock outcrops, the interpretive notations for regions among the spatial coordinates associated with the plurality of the observed rock outcrop features of the at least two rock outcrops, and
estimating, based on the interpolation, modulation of the reservoir boundaries of the plurality of outcrops;
transmit, by the mobile computing device, the generated reservoir modulation trend to a three-dimensional reservoir interpretation system;
generate using the reservoir modulation trend, a three-dimensional lithofacies model of the region; and
drill one or more wells based on the three-dimensional lithofacies model.

16. The system of claim 15, further configured to receive at least one well core image with the mobile computing device.

17. The system of claim 16, further configured to interpret the received at least one well core image using an application executing on the mobile computing device.

18. The system of claim 17, further configured to garner a digital well core representation from the at least one well core image.

19. The system of claim 18, further configured to:
generate a well core correlation from a plurality of digital well core interpretations; and
transmit the well core correlation to the three-dimensional reservoir interpretation system.

20. The system of claim 19, wherein the well core correlation is used with the generated reservoir modulation trend to generate the three-dimensional lithofacies model.

* * * * *